United States Patent [19]

Schulz

[11] 4,204,431
[45] May 27, 1980

[54] DEVICE FOR TEMPERATURE MEASUREMENT AND SAMPLING OF A STEEL

[75] Inventor: Herbert Schulz, Rosenheim, France

[73] Assignee: Creusot-Loire Enterprises, Courbevoie la Defense, France

[21] Appl. No.: 969,056

[22] Filed: Dec. 13, 1978

[30] Foreign Application Priority Data

Dec. 29, 1977 [FR] France ............................... 77 39548

[51] Int. Cl.² ............................................. G01N 1/12
[52] U.S. Cl. ............................. 73/423 R; 73/DIG. 9
[58] Field of Search .................... 73/425.4 R, 425.6 R, 73/DIG. 9; 164/4; 73/423 R

[56] References Cited

U.S. PATENT DOCUMENTS

| | | | |
|---|---|---|---|
| 3,490,289 | 1/1970 | Mangin | 73/DIG. 9 |
| 3,638,500 | 2/1972 | Wetzel | 73/DIG. 9 |
| 3,717,034 | 2/1973 | Dukelow | 73/DIG. 9 |
| 3,916,693 | 11/1975 | Haneart et al. | 73/DIG. 9 |
| 4,003,261 | 1/1977 | Nautet | 73/DIG. 9 |

FOREIGN PATENT DOCUMENTS 50-36802 11/1975 Japan .................................. 73/DIG. 9

*Primary Examiner*—S. Clement Swisher
*Attorney, Agent, or Firm*—Haseltine, Lake & Waters

[57] ABSTRACT

The measurement of temperature and the sampling of a steel bath in a converter are effected using a remotely controlled device comprising a composite probe or two probes for temperature measurement and sampling, the probe being mounted on the end of a measurement rod fixed to the end telescopic element of a telescopic jack which is pivotally mounted on a carriage mounted for movement on a support suspended above the working platform of the converter. The carriage is horizontally movable between a storage position and a position opposite the mouth of the converter and the jack is pivotal in a vertical plane between a vertical storage position and an inclined operative position with the converter. All movements of the jack and carriage are remotely controlled.

15 Claims, 8 Drawing Figures

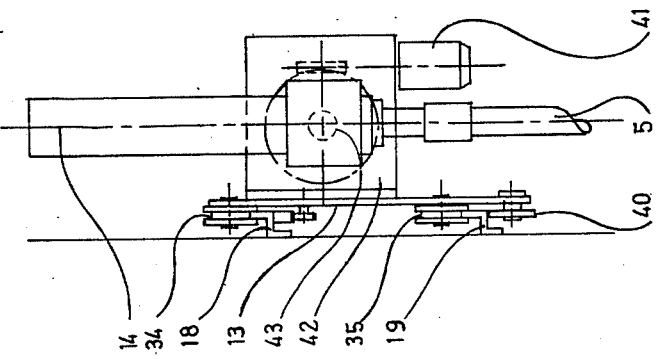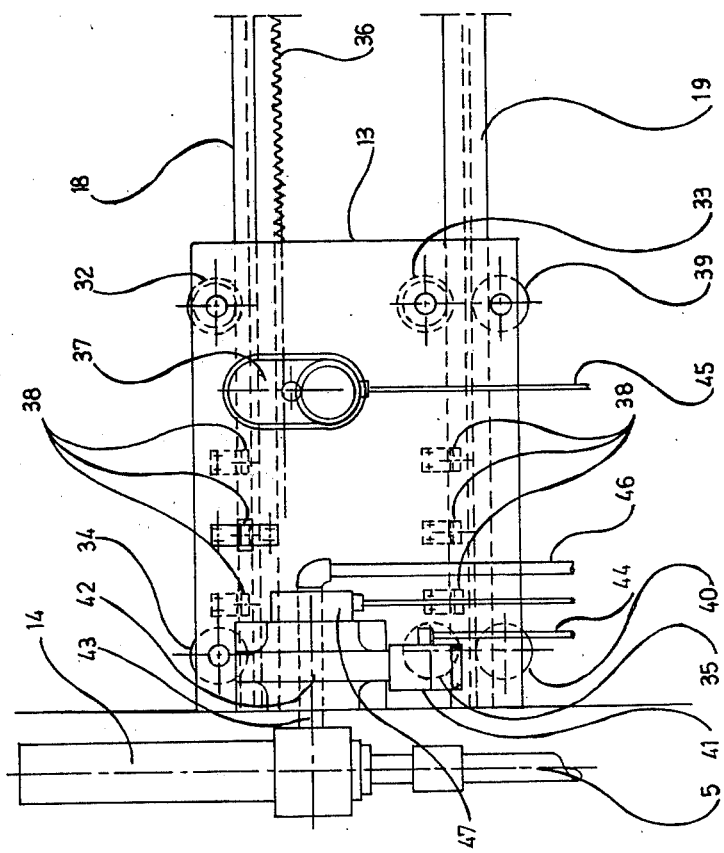

DEVICE FOR TEMPERATURE MEASUREMENT AND SAMPLING OF A STEEL

FIELD OF THE INVENTION

The present invention relates to a device which makes it possible to mechanize the present manual operations for temperature measurement and/or sampling of the bath of steel in a converter, at the end of the operation for converting liquid pig iron into steel.

PRIOR ART

It is known that, at the end of the oxygenation operation, and before it is possible to cast the steel obtained in the converter, it is essential to carry out two checks:

a check of the temperature of the liquid bath of steel, and a check of the chemical composition of the bath.

At the present time, the temperature check is carried out using a thermocouple placed in a cardboard cartridge which is lowered by an operator into the bath, after the cartridge has been placed at the end of a long steel rod into which the electric wires connected to the thermocouple pass. The most widespread method of doing this consists in tilting the converter, the oxygenation being stopped, and then, from the working platform, lowering the rod into the bath of steel, after having passed it through the layer of slag.

In order to carry out the chemical composition check, it is necessary to take a sample of the bath and to perform a chemical analysis thereof, for example by spark analysis. This sampling is carried out by dipping another long steel rod into the bath of the converter when tilted, from the working platform, the end of the rod being equipped with a mould for collecting the sample. Again, in this case, it is first necessary to pass the rod through the layer to lower the slag rod into the bath.

With the capacity of the converters which are currently used, these two measurement rods have reached such a length (which can range up to five meters) that two workers are required to manipulate them. Moreover, in order to pass a rod through the slag layer, it is necessary to incline and lower the rod, and this demands a considerable physical effort which is made even more arduous because of the very high temperature which prevails. Furthermore, the difficulty involved in this operation necessarily makes the latter rather slow, regardless of the expertise of the operators. This therefore prolongs the measurement time, and hence the time between castings, and consequently increases the cost of the steel obtained.

It is currently proposed, for converters using pure oxygen blown through the mouth, such as "LD" converters, to provide a vertical lance for temperature measurement, which lance is parallel to the oxygen lance. However, the device requires a second hole in the hood and this is accompanied by the corresponding problems of leaktightness and hence of rather high investment. Furthermore, this proposal does not solve the problem of sampling, which must be carried out, as above, by manual operation with the converter in an inclined position. Finally, when employing a converter using pure oxygen blown through the bottom, such as a "LWS" or "OBM" converter, it is obviously only possible to carry out the measurements with the converter in an inclined position, in order to prevent the liquid steel from penetrating into the oxygen blast-nozzles.

SUMMARY OF THE INVENTION

It is an object of the present invention to provide a device which makes it possible to achieve total mechanization of the two measurements, regardless of the type of converter used.

According to the invention there is provided a device for temperature measurement and sampling of a molten steel bath in a converter having a working platform and when said converter is in a position inclined towards said platform, said device comprising:

support means suspended above said working platform;

a carriage;

means mounting said carriage on said support means for movement horizontally relative thereto;

drive means for moving said carriage on said support means;

a telescopic jack comprising a plurality of telescopic elements;

means mounting said jack on said carriage for pivotal movement relative thereto in a vertical plane;

drive means for pivoting said jack on said carriage;

a measurement rod mounted on the end one of said telescopic elements in alignment therewith;

a probe means adapted for temperature measurement and for sampling and for mounting at the end of said measurement rod; and remote control means for actuating said jack, and for actuating said drive means of said jack and of said carriage.

Advantageously, for maximizing the saving in measurement time, the probe means is adapted for simultaneous temperature measurement and sampling.

The invention will be more fully understood from the following description of an embodiment thereof, given by way of example only, with reference to the accompanying drawings.

BRIEF DESCRIPTION OF THE DRAWING

In the drawings:

FIG. 4A is a diagrammatic front view of the carriage of the device of FIG. 1;

FIG. 4B is a diagrammatic elevation view of the carriage;

DETAILED DESCRIPTION

Figure 1:
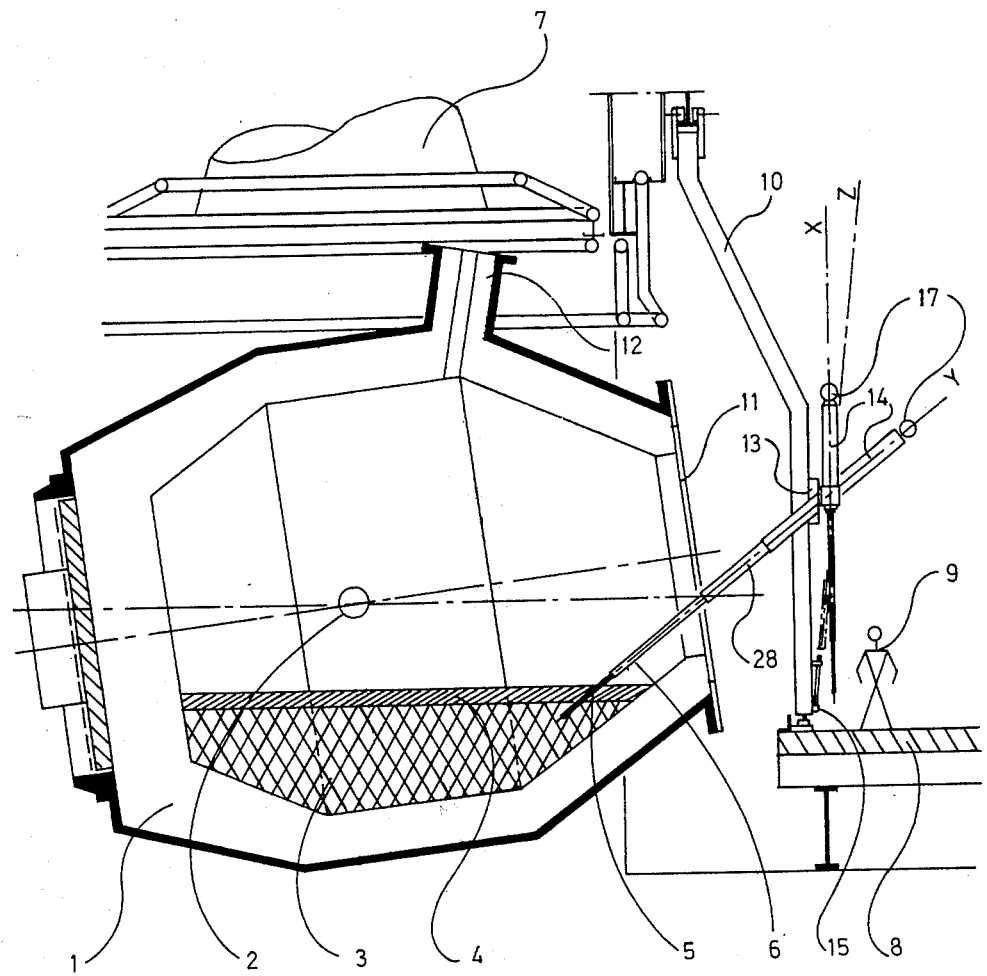
FIG. 1 is a diagrammatic view, partly in section, of an embodiment of a device according to the invention during operation of a converter.

FIG. 1 shows a converter 1 which has been tilted about its axis 2 to enable the temperature measurement and sampling to be carried out. The converter is provided with a hood 7, which is adapted to receive fumes from the converter. The converter contains a bath 3 of liquid steel with a layer 4 of slag on top of the bath 3.

Motorized, sliding protective doors 10, which make it possible to gain access to the mouth 11 of the converter 1 when the latter is in the inclined position, shown in FIG. 1, rest on a working platform 8, on which an operator 9 can be seen. In addition to the mouth 11, the converter 1 possesses an outlet 12 for liquid steel to be cast.

A carriage 13, which is movable horizontally and supports a telescopic jack 14, the inclination of which can be adjusted in a vertical plane, is fixed to a support 10 which is either fixed to the sliding door 10, as shown, or fixed to the roof above the working platform 8. A measurement rod 6, which is of a conventional type but has a reduced length, is fixed to the end of the last telescopic element 28 of the jack 14 and itself carries, at its end, a probe or cartridge 5 for temperature measurement and/or sampling.

FIG. 1 shows three different positions X, Y and Z of the measurement assembly comprising jack 14, rod 6 and probe or cartridge 5:

the position X is the vertical rest position of the assembly;

the substantially inclined position Y is the working position of the assembly; and the slightly inclined position Z corresponds to a position in which the probe 5 is removed after sampling has been carried out, the probe then being locked in a motorized vise 15, and the position in which a new probe is placed in position.

At the head of the body of the jack 14, there is a reel 17 for an electrical measurement cable which is connected to the thermocouple, for temperature measurement, located in the probe 5 intended for temperature measurement.

Figure 2:
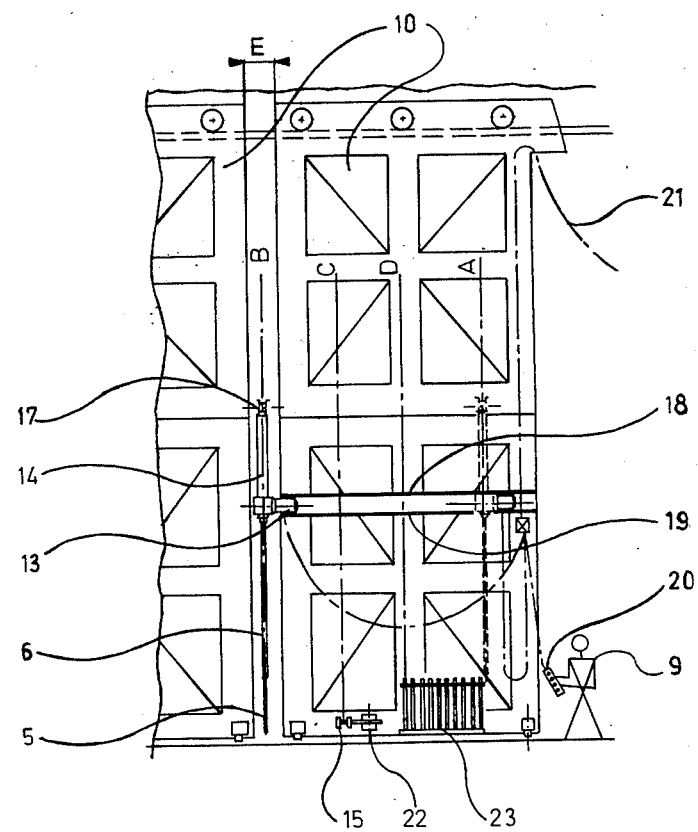
FIG. 2 is a diagrammatic elevation view of the device of FIG. 1, seen from the working platform.

In FIG. 2, the sliding protective doors 10 can be seen which are simply opened to provide a gap E sufficient to allow passage of the measurement assembly. The position B of the assembly, shown in FIG. 2, corresponds to its working position.

The carriage 13 supporting the measurement assembly is movable horizontally on two rails 18 and 19. All the movements are remote-controlled by the operator 9, by a manual control box 20 and an electrical power supply 21.

Mounted on the platform 8 are a grinding wheel 22 for cutting a mould containing the sample and a supply 23 of new probes which are ready for use. Position C of the measurement assembly represents the position for dismantling the probe, position D represents the position for taking up another probe and position A represents the storage position of the measurement assembly during the active period of oxygenation of the pig iron.

Figure 3:
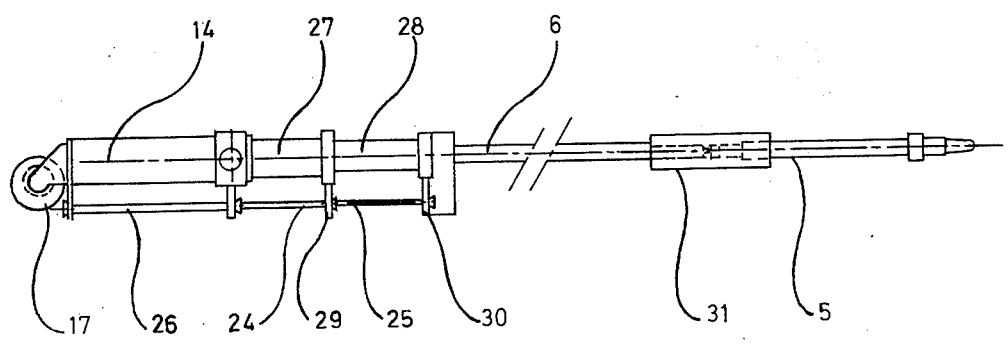
FIG. 3 is a diagrammatic side view of the telescopic assembly of jack, measurement rod and probe of the device of FIG. 1, in the open position.

FIG. 3 shows the telescopic measurement assembly in greater detail. The assembly comprises:

the telescopic jack 14 which comprises a fixed body connected to a compressed air inlet (not shown), and a plurality of telescopic elements, e.g. elements 27 and 28;

a measurement rod 6 fixed to the end of the last telescopic element 28;

a probe 5 comprising a female part 31, which is permanently fixed to the end of the rod 6, and a male cartridge for temperature measurement and/or sampling; and an auxiliary telescopic tube having a fixed element 26 and a plurality of movable elements, e.g. elements 24 and 25, which are respectively driven by the elements 27 and 28 of the main jack by means of coupling pieces (29 and 30); this auxiliary telescopic tube is hollow and contains the electrical cable which is connected to the thermocouple, which is placed in the cartridge 5 when the latter is intended for temperature measurement or a composite sampling/temperature measuring cartridge, and to a temperature recorder, which is placed, for example, on the working platform.

The extended length of the telescopic jack 14 with its elements 27 and 28, and also that of the rod 6, can be several meters, depending on the size of the converter.

FIGS. 4A and 4B show, in greater detail, the carriage 13, on which the measurement assembly is mounted, a front view being shown in FIG. 4A and an elevation view in FIG. 4B.

The carriage 13 moves along the rails 18 and 19 on four wheels 32, 33, 34 and 35 and is driven horizontally along the rails 18, 19 by a toothed-wheel device which is driven by a motor reducer 37 along a rack 36. The carriage 13 is guided in its movement by guide elements 38, e.g. rollers, the carriage being prevented from tilting by elements 39 and 40, e.g. check pulleys. A motor reducer set 41 and 42 with a bevel gear controls the movement of the jack 14 about a horizontal axis 43 in the vertical plane. The lines 44, and 45 are respective electrical power lines for line 46 serves for motors 41 and 37 and the compressed air supply for the jack 14. An angle coder 47 may, if desired, be connected to the motor reducer set 41 and 42 to enable it to be controlled by a program. Likewise, another coder (not shown) can be connected to the motor reducer set 37 to enable control of the movement of the carriage in the horizontal plane, by a program, if desired.

Figure 5:
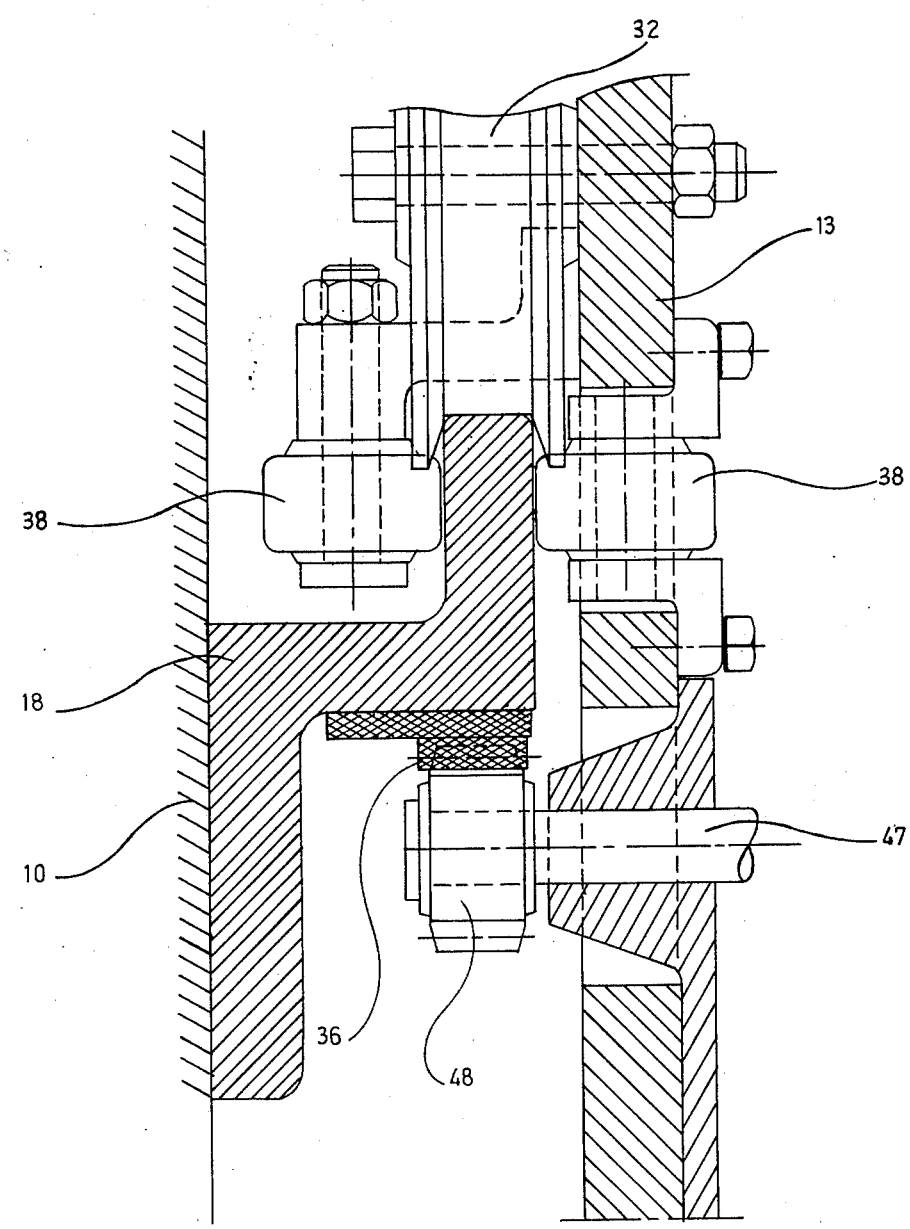
FIG. 5 shows a detail in section of the drive means for the carriage of FIG. 4.

FIG. 5 is a view in elevation of the rear upper part of the carriage 13 showing the device for driving the carriage. The upper rail 18, as shown welded to the rear of the door 10, or, if not to the door, to a support placed on the working platform or suspended thereabove, the rack 36, a toothed drive wheel 48 engaging the rack and coupled by a shaft 47 to the motor reducer set 37, in FIG. 4, can be clearly seen.

The device shown in FIGS. 1 to 5 makes it possible to substantially reduce the work of the personnel in steelworks during temperature measurement and sampling operations, and also to reduce the time required for these operations. This operating time may also be reduced further by carrying out the two measurements in a single operation, using a composite probe.

Figure 6:
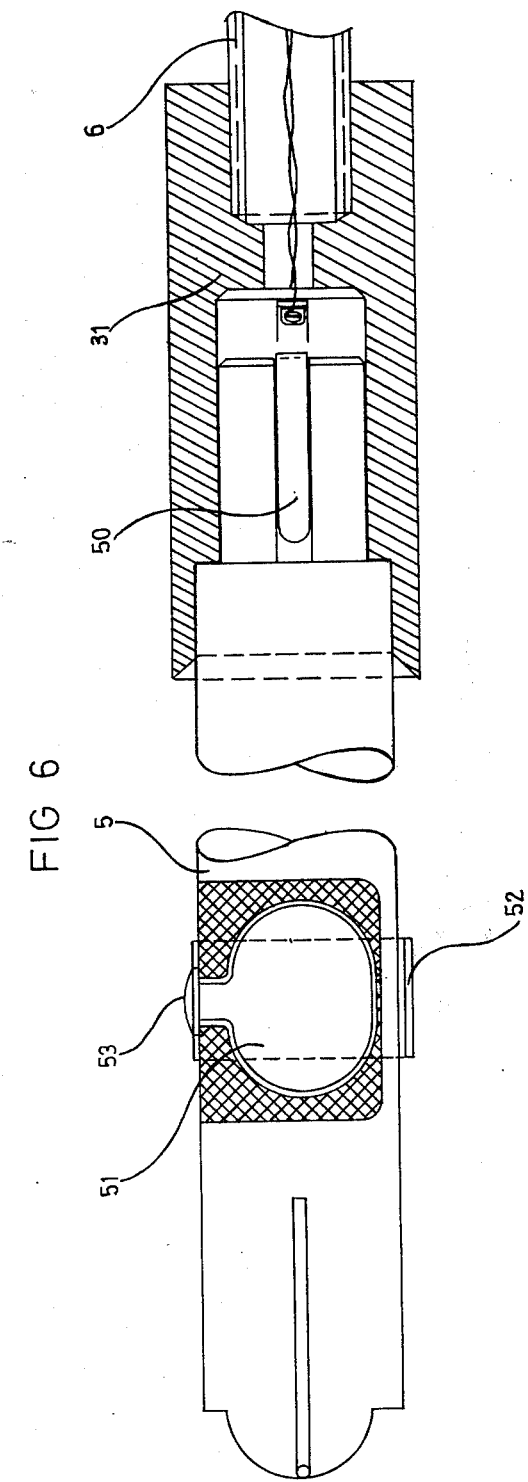
FIG. 6 is a side view of a composite probe for the device of FIG. 1.
Figure 7:
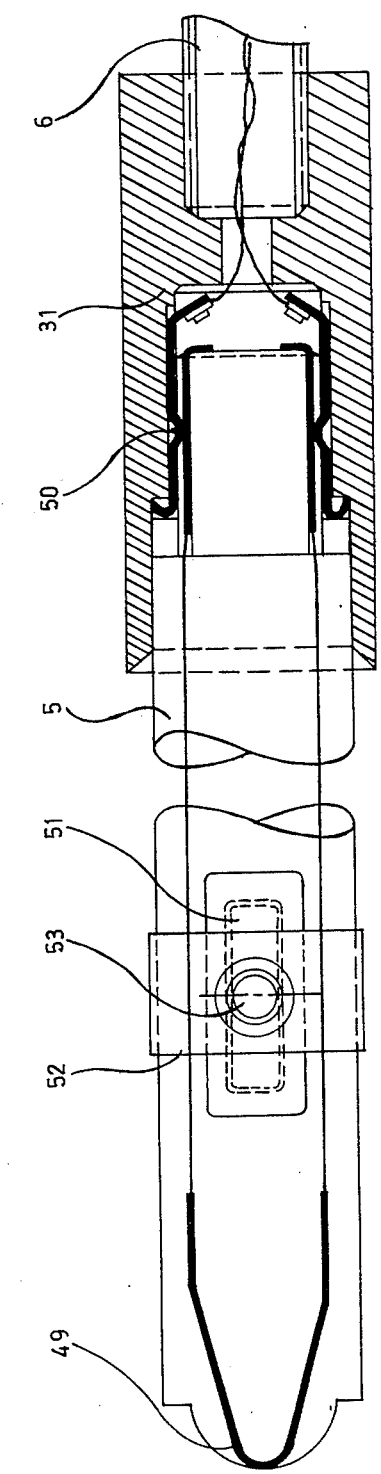
FIG. 7 is a top view of the probe of FIG. 6.

FIGS. 6 and 7 respectively show a side view and a top view of such a composite probe. This probe comprises a female part 31 which is fast with the rod 6, and a male part or cartridge 5 which fits into the part 31. The fixed part 31 comprises an electrical contact 50 for the thermocouple. The movable part of probe 5, which is advantageously made of a ceramic material, comprises a thermocouple 49 for temperature measurement, and a mould 51 for collecting the sample and which is advantageously equipped with a fusible protective cap 53. The sampling mould 51 is held in position in the cartridge by means of a ring 52 which is provided with a hole in alignment with the cap 53. In a manner which is in itself known, the material forming the protective cap 53, which is of a type in common use at the present time, is such that it melts in the molten steel but does not melt during its passage through the slag which is at a lower temperature.

The above described device operates in the following manner, it being assumed that it is equipped with a composite probe as shown in FIGS. 6 and 7.

With the converter at the oxygenation stage, the doors 10 are closed and the measurement assembly is in the storage position A (FIG. 2), that is to say as far as possible from the bath of metal. A composite measurement probe 5 is fitted to the end of the rod 6, ready for use.

When the oxygenation stage has ended, the converter is tilted, as shown in FIG. 1, the lance being simultaneously brought into the working position B, and the motorized sliding doors 10 are then opened to provide the gap E which is sufficient to allow the measurement rod to pass through.

The telescopic measurement assembly is then rotated by devices 41 and 42 from the vertical position X to the position Y, so that the telescopic assembly is directed towards the bath of steel in the converter.

An electric valve, which is placed, for example, on the control box 20 and controls the intake 46 for compressed air to the jack is then actuated to cause the telescopic elements 27 and 28 to be extended and this causes the rod 6 and the measurement probe 5 to move towards the bath of steel 3. When the measurement probe 5 touches the surface of the slag 4, the resistance encountered causes a pulse in the compressed air circuit, and this gives the order to pass through the layer of slag with a predetermined force (generally 100 to 130 kgf), so as to permit a gentle lowering of the probe to a determined penetration depth which is sufficient for the probe 5 to be completely immersed in the bath of liquid steel. This sequence is carried out in a simple manner using a conventional device with electrovalves and a timer.

After having recorded the temperature and having left the probe in the bath for the time required to fill the mould 51, the probe is withdrawn by retracting the telescopic elements 27, 28, and the measurement assembly is brought back into the vertical position and the sliding doors are then closed. The carriage 13 is then moved into position C, where the device 15, 22, for removing the movable part of probe 5, is located. In order to remove the movable part of probe 5, the telescopic assembly is rotated to position Z (FIG. 1), and this makes it possible to insert the end of the probe 5 in the motorized vise 15 which closes on command and locks on to the probe. The movable part of the probe 5 is then withdrawn from the rod 6 by acting on the telescopic jack to raise the rod 6.

The vise 15 is equipped with double motorised grinding wheel 22, by which the part of the probe which contains the sample is cut off. It is then possible to open the vise and withdraw the sample manually in order to send it to the laboratory. While this removal operation is being carried out, the measurement assembly is returned to the vertical position X and the carriage moved to position D in order to take up a new probe.

The carriage is moved so that the free end of the rod 6 is above the tip of the first available probe 23, the telescopic assembly is inclined to position Z and, by acting on the jack to extend the jack, the probe is inserted into the fixed part 31 at the end of the rod 6. The locking mechanism holding the new probe in the storage position is then released and the measurement assembly resumes the vertical position X and is moved into the storage position A until it is required to be used again.

All the operations described above can be manually remote-controlled by the operator 9 using the control box 20. It is obviously also possible to effect a complete automation of all these operations using the coders described above and a commercially available sequential programming device.

The invention finds its application in the field of metallurgy.

What is claimed is:

1. A device for temperature measurement and sampling of a molten steel bath in a converter having a working platform adjacent thereto, the measurement and sampling being effected when said converter is in a position inclined towards said platform, said device comprising:
   support means suspended above said working platform in spaced relation therewith;
   a carriage;
   means mounting said carriage on said support means for movement horizontally relative thereto;
   drive means for moving said carriage on said support means;
   a telescopic jack comprising a plurality of telescopic elements;
   means mounting said jack on said carriage for pivotal movement relative thereto in a vertical plane;
   drive means for pivoting said jack on said carriage;
   a measurement rod mounted on the end one of said telescopic elements in alignment therewith;
   a probe means for temperature measurement and for sampling mountable at the end of said measurement rod;
   remote control means for actuating said jack, and for actuating said drive means of said jack and of said carriage; and
   at least one protective sliding door extending above said platform and facing said converter, said telescopic jack having a vertical rest position above said platform and adjacent said door on the side thereof remote from said converter.

2. A device as claimed in claim 1, wherein said support means is mounted on said door.

3. A device as claimed in claim 1, wherein said probe means serves for simultaneous sampling and temperature measurement.

4. A device as claimed in claim 1, wherein said probe means comprises a first probe for temperature measurement and a second probe for sampling, said first and second probes being mounted separately and sequentially on said end of said measurement rod.

5. A device as claimed in claim 1, wherein said drive means includes coders for program control thereof.

6. A device as claimed in claim 1, wherein said probe means is removably mounted on said end of said measurement rod.

7. A device as claimed in claim 1, wherein said support means is suspended at a level above the working platform to provide considerable overhead clearance for a person standing on the platform.

8. A device as claimed in claim 1, comprising means on said platform for supporting replacement probe means thereon, said carriage being horizontally movable to a position adjacent the support means for the replacement probe means to enable replacement of the probe means on said telescopic jack.

9. A device as claimed in claim 8 comprising vise means on said platform for engaging the probe means on the telescopic jack to hold the probe means upon removal thereof from said jack.

10. A device as claimed in claim 9 wherein said jack is in pivoted position towards said door with the probe means engaged in said vise means.

11. A method for using the device as claimed in claim 1 for at least one of the operations of temperature measurement and sampling of a bath of steel in a converter at the end of the conversion operation thereof, comprising:

during the period of activation of pig iron in said converter, placing said carriage with said jack and rod in a storage position A remote from said converter;

when the oxygenation stage has ended, tilting said converter in the direction of said measurement platform, simultaneously bringing said carriage with said jack, rod and probe means to a working position B opposite the mouth of said converter, pivoting said jack so as to direct it towards the bath of steel in said converter, extending said jack so that said rod, equipped with said probe means, is moved forward until said probe means penetrates the bath of steel;

when the temperature of the bath has been recorded and/or a sample has been taken, retracting said jack and pivoting said jack to its initial position;

removing said probe means; and fixing a new probe means to said end of said measurement rod.

12. A method as claimed in claim 11 comprising moving said sliding door to provide a gap opposite the converter mouth sufficient to permit said measurement rod and probe means to pass therethrough.

13. A method as claimed in claim 11, wherein after a new probe means has been fixed to said end of said measurement rod, said carriage is returned to said storage position.

14. A method as claimed in claim 11, wherein said probe means comprises at least one of a temperature probe and a sampling probe, said new probe means being the other of said probes, and, after said new probe means has been fixed to said measurement rod, placing said jack in said working position B and effecting the second measurement and returning said carriage to said storage position after said second measurement has been effected.

15. A device as claimed in claim 1 wherein said sliding door has a closed position and said telescopic jack occupies said vertical rest position adjacent thereto, said door being openable to form a gap through which said telescopic jack can be extended and pivoted to an operative inclined position with respect to the vertical.

* * * * *